(12) United States Patent
Bailey (10) Patent No.: US 9,596,839 B2
(45) Date of Patent: Mar. 21, 2017

(54) MOTION CAPTURE WHILE FISHING (71) Applicant: Navico Holding AS, Egersund (NO)

(72) Inventor: Paul Robert Bailey, Auckland (NZ)

(73) Assignee: NAVICO HOLDING AS, Egersund (NO)

( * ) Notice: Subject to any disclaimer, the term of this patent is extended or adjusted under 35 U.S.C. 154(b) by 100 days.

(21) Appl. No.: 14/461,394

(22) Filed: Aug. 16, 2014

(65) Prior Publication Data

US 2015/0055827 A1  Feb. 26, 2015

Related U.S. Application Data

(60) Provisional application No. 61/868,444, filed on Aug. 21, 2013.

(51) Int. Cl.
*G06T 7/00* (2006.01)
*A01K 97/00* (2006.01)
(Continued)

(52) U.S. Cl.
CPC .............. *A01K 97/00* (2013.01); *A01K 79/00* (2013.01); *A01K 99/00* (2013.01); *A61B 5/1118* (2013.01); *A61B 5/1123* (2013.01); *G01B 21/00* (2013.01); *G01C 21/20* (2013.01); *G01C 21/203* (2013.01); *G06F 3/014* (2013.01); *G06F 3/017* (2013.01); *G06F 3/0231* (2013.01); *G06F 3/0346* (2013.01); *G06F 11/3438* (2013.01); *G06F 11/3476* (2013.01); *G06F 15/0225* (2013.01); *G06F 17/30867* (2013.01); *G06K 9/00342* (2013.01); *G06Q 10/00* (2013.01); *G06Q 50/01* (2013.01); *G06T 7/2033* (2013.01);
(Continued)

(58) Field of Classification Search
CPC ..... A01K 97/00; G06T 7/2093; G06T 7/2033; G06T 7/60; G06T 2207/10016
See application file for complete search history.

(56) References Cited

U.S. PATENT DOCUMENTS 4,829,493 A   5/1989   Bailey
4,879,697 A   11/1989  Lowrance et al.
(Continued)

FOREIGN PATENT DOCUMENTS

DE   102004059619 A1   6/2006
EP   1 561 377 A1      8/2005
(Continued)

OTHER PUBLICATIONS

Howard McElderry, "At-Sea Observing Using Video-Based Electronic Monitoring" Prepared For: Electronic Monitoring Workshop Jul. 29-30, 2008.*
(Continued)

*Primary Examiner* — Utpal Shah
(74) *Attorney, Agent, or Firm* — Nelson Mullins Riley & Scarborough LLP (57) ABSTRACT

Various implementations described herein are directed to a non-transitory computer readable medium having stored thereon computer-executable instructions which, when executed by a computer, may cause the computer to automatically receive motion capture data recorded by one or more cameras. The computer may analyze the motion capture data to detect a cast, catch, or bite. The computer may store a record of the cast, catch, or bite.

19 Claims, 7 Drawing Sheets (51) Int. Cl.

| | | |
|---|---|---|
| *H04N 5/232* | (2006.01) | |
| *H04N 5/91* | (2006.01) | |
| *H04N 21/4335* | (2011.01) | |
| *G08C 17/02* | (2006.01) | |
| *G06F 3/01* | (2006.01) | |
| *G06F 3/023* | (2006.01) | |
| *G06F 15/02* | (2006.01) | |
| *G06T 11/20* | (2006.01) | |
| *G06T 7/20* | (2006.01) | |
| *G06T 7/60* | (2006.01) | |
| *G11B 27/031* | (2006.01) | |
| *G11B 27/17* | (2006.01) | |
| *G11B 31/00* | (2006.01) | |
| *A01K 99/00* | (2006.01) | |
| *G01C 21/20* | (2006.01) | |
| *A61B 5/11* | (2006.01) | |
| *G01B 21/00* | (2006.01) | |
| *G06Q 10/00* | (2012.01) | |
| *G06Q 50/00* | (2012.01) | |
| *G06F 17/30* | (2006.01) | |
| *A01K 79/00* | (2006.01) | |
| *G06F 11/34* | (2006.01) | |
| *G06K 9/00* | (2006.01) | |
| *G11B 27/28* | (2006.01) | |
| *G11B 27/34* | (2006.01) | |
| *G06F 3/0346* | (2013.01) | |
| *H04Q 9/00* | (2006.01) | |
| *B63B 49/00* | (2006.01) | |
| *G01S 15/96* | (2006.01) | |
| *G06F 11/30* | (2006.01) | |
| *G01S 7/00* | (2006.01) | |

(52) U.S. Cl.
CPC ............. *G06T 7/2093* (2013.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04N 5/232* (2013.01); *H04N 5/91* (2013.01); *H04N 21/4335* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01); *G06T 2207/30196* (2013.01); *G08C 2201/32* (2013.01); *H04Q 2209/43* (2013.01); *Y02B 60/165* (2013.01)

(56) References Cited

U.S. PATENT DOCUMENTS

| | | | |
|---|---|---|---|
| 5,025,423 | A | 6/1991 | Earp |
| 5,191,341 | A | 3/1993 | Gouard et al. |
| 5,321,391 | A | 6/1994 | Fox |
| 5,446,775 | A | 8/1995 | Wright et al. |
| 5,537,380 | A | 7/1996 | Sprankle, Jr. et al. |
| 5,546,695 | A | 8/1996 | Langer |
| 6,222,449 | B1 | 4/2001 | Twining |
| 6,225,984 | B1 | 5/2001 | Crawford |
| 6,252,544 | B1 | 6/2001 | Hoffberg |
| 6,263,147 | B1 | 7/2001 | Tognazzini |
| 6,321,158 | B1 | 11/2001 | DeLorme et al. |
| 6,411,283 | B1 | 6/2002 | Murphy |
| 6,418,080 | B2 | 7/2002 | Inouchi |
| 6,421,299 | B1 | 7/2002 | Betts et al. |
| 6,459,372 | B1 | 10/2002 | Branham et al. |
| 6,567,792 | B1 | 5/2003 | Arnold |
| 6,584,722 | B1 | 7/2003 | Walls |
| 6,587,740 | B2 | 7/2003 | Byrne et al. |
| 6,751,626 | B2 | 6/2004 | Brown et al. |
| 6,761,692 | B2 | 7/2004 | Angelsen et al. |
| 6,798,378 | B1 | 9/2004 | Walters |
| 6,816,782 | B1 | 11/2004 | Walters et al. |
| 7,002,579 | B2 | 2/2006 | Olson |
| 7,236,426 | B2 | 6/2007 | Turner et al. |
| 7,243,457 | B1 | 7/2007 | Smith et al. |
| 7,319,992 | B2 | 1/2008 | Gaos |
| 7,321,824 | B1 | 1/2008 | Nesbitt |
| 7,430,461 | B1 | 9/2008 | Michaels |
| 7,652,952 | B2 | 1/2010 | Betts et al. |
| 7,710,825 | B2 | 5/2010 | Betts et al. |
| 7,722,218 | B2* | 5/2010 | Leung .................... A01K 85/01 362/253 |
| 7,729,203 | B2 | 6/2010 | Betts et al. |
| 7,755,974 | B2 | 7/2010 | Betts et al. |
| 7,812,667 | B2 | 10/2010 | Fagg |
| 7,870,496 | B1 | 1/2011 | Sherwani |
| 7,890,867 | B1 | 2/2011 | Margulis |
| 8,019,532 | B2 | 9/2011 | Sheha et al. |
| 8,040,758 | B1 | 10/2011 | Dickinson |
| 8,063,540 | B2 | 11/2011 | Angelsen et al. |
| 8,452,797 | B1 | 5/2013 | Paleja et al. |
| 8,468,164 | B1 | 6/2013 | Paleja et al. |
| 2001/0054961 | A1 | 12/2001 | Twining |
| 2002/0035574 | A1 | 3/2002 | Dumas |
| 2002/0093541 | A1 | 7/2002 | Schileru-Key |
| 2002/0099457 | A1 | 7/2002 | Fredlund et al. |
| 2002/0116421 | A1 | 8/2002 | Fox et al. |
| 2003/0046689 | A1 | 3/2003 | Gaos |
| 2003/0056419 | A1 | 3/2003 | Squires et al. |
| 2003/0089020 | A1 | 5/2003 | Dirito |
| 2004/0124297 | A1 | 7/2004 | Steer |
| 2004/0162830 | A1 | 8/2004 | Shirwadkar et al. |
| 2004/0193364 | A1 | 9/2004 | Chojnacki |
| 2004/0249860 | A1 | 12/2004 | Stechschulte et al. |
| 2005/0037872 | A1 | 2/2005 | Fredlund et al. |
| 2005/0102101 | A1 | 5/2005 | Beesley et al. |
| 2006/0013066 | A1 | 1/2006 | Nishimori et al. |
| 2006/0048434 | A1 | 3/2006 | Congel |
| 2006/0119585 | A1 | 6/2006 | Skinner |
| 2006/0224940 | A1 | 10/2006 | Lee |
| 2006/0265931 | A1 | 11/2006 | McFadden et al. |
| 2007/0011334 | A1 | 1/2007 | Higgins et al. |
| 2007/0045010 | A1 | 3/2007 | Kasperek |
| 2007/0058489 | A1 | 3/2007 | Bratcher |
| 2007/0220798 | A1 | 9/2007 | Davidson |
| 2008/0126935 | A1 | 5/2008 | Blomgren |
| 2008/0165022 | A1 | 7/2008 | Herz et al. |
| 2008/0204424 | A1 | 8/2008 | Jin et al. |
| 2008/0246627 | A1 | 10/2008 | Guazzelli |
| 2009/0064055 | A1 | 3/2009 | Chaudhri et al. |
| 2009/0099871 | A1 | 4/2009 | Gadodia |
| 2009/0105952 | A1 | 4/2009 | Grace et al. |
| 2009/0179789 | A1 | 7/2009 | Haughay, Jr. et al. |
| 2009/0240354 | A1 | 9/2009 | Davidson |
| 2009/0241636 | A1 | 10/2009 | Obori |
| 2009/0249247 | A1 | 10/2009 | Tseng et al. |
| 2009/0258710 | A1 | 10/2009 | Quatrochi |
| 2009/0271054 | A1 | 10/2009 | Dokken |
| 2009/0287409 | A1 | 11/2009 | Summers |
| 2009/0295626 | A1 | 12/2009 | Su |
| 2010/0049468 | A1 | 2/2010 | Papadourakis |
| 2010/0080082 | A1 | 4/2010 | Betts et al. |
| 2010/0145601 | A1 | 6/2010 | Kurtti et al. |
| 2010/0199225 | A1 | 8/2010 | Coleman et al. |
| 2010/0226203 | A1 | 9/2010 | Buttle et al. |
| 2010/0250122 | A1 | 9/2010 | Kubota et al. |
| 2010/0319235 | A1* | 12/2010 | Panaro .................... A01K 97/00 43/26.1 |
| 2011/0007035 | A1 | 1/2011 | Shai |
| 2011/0013484 | A1 | 1/2011 | Coleman et al. |
| 2011/0013485 | A1 | 1/2011 | Maguire |
| 2011/0019887 | A1 | 1/2011 | Roehrig et al. |
| 2011/0025720 | A1 | 2/2011 | Jo et al. |
| 2011/0067290 | A1 | 3/2011 | Miskatovic |
| 2011/0082644 | A1 | 4/2011 | Imasaka et al. |
| 2011/0154183 | A1 | 6/2011 | Burns et al. |

(56) References Cited

U.S. PATENT DOCUMENTS

| | | |
|---|---|---|
| 2011/0208479 A1 | 8/2011 | Chaves |
| 2011/0213515 A1 | 9/2011 | Haymart et al. |
| 2011/0214500 A1 | 9/2011 | Cabrera et al. |
| 2011/0257819 A1 | 10/2011 | Chen et al. |
| 2012/0001773 A1 | 1/2012 | Lyons et al. |
| 2012/0011437 A1 | 1/2012 | James et al. |
| 2012/0014220 A1 | 1/2012 | DePasqua |
| 2012/0047790 A1 | 3/2012 | Hess et al. |
| 2012/0069712 A1 | 3/2012 | Potanin et al. |
| 2012/0106300 A1 | 5/2012 | Maguire |
| 2012/0144384 A1 | 6/2012 | Baek |
| 2012/0144723 A1 | 6/2012 | Davidson |
| 2012/0185801 A1 | 7/2012 | Madonna et al. |
| 2012/0316456 A1 | 12/2012 | Rahman et al. |
| 2012/0316458 A1 | 12/2012 | Rahman et al. |
| 2012/0317167 A1 | 12/2012 | Rahman et al. |
| 2013/0007665 A1 | 1/2013 | Chaudhri et al. |
| 2013/0040714 A1 | 2/2013 | Rosing |
| 2013/0074051 A1 | 3/2013 | Freeman |
| 2013/0096575 A1 | 4/2013 | Olson |
| 2013/0107031 A1 | 5/2013 | Atkinson |
| 2013/0281087 A1 | 10/2013 | Ruhanen et al. |
| 2013/0307720 A1 | 11/2013 | Lilburn |
| 2013/0343151 A1 | 12/2013 | Shiraki et al. |
| 2014/0012587 A1 | 1/2014 | Park |
| 2014/0032468 A1 | 1/2014 | Anandaraj |
| 2014/0071059 A1 | 3/2014 | Girault |
| 2014/0111368 A1 | 4/2014 | Lee et al. |
| 2014/0180566 A1 | 6/2014 | Malhotra |
| 2014/0195297 A1 | 7/2014 | Abuelsaad et al. |
| 2014/0358483 A1 | 12/2014 | da Rosa |
| 2015/0019135 A1* | 1/2015 | Kacyvenski ......... A61B 5/0488 702/19 |
| 2015/0051786 A1 | 2/2015 | Wang |
| 2015/0054655 A1 | 2/2015 | Bailey |
| 2015/0054732 A1 | 2/2015 | Bailey |
| 2015/0054828 A1 | 2/2015 | Bailey |
| 2015/0054829 A1 | 2/2015 | Bailey |
| 2015/0055827 A1 | 2/2015 | Bailey |
| 2015/0055930 A1 | 2/2015 | Bailey |
| 2015/0057929 A1 | 2/2015 | Bailey |
| 2015/0057965 A1 | 2/2015 | Gaynor |
| 2015/0057968 A1 | 2/2015 | Bailey |
| 2015/0058020 A1 | 2/2015 | Bailey |
| 2015/0058237 A1 | 2/2015 | Bailey |
| 2015/0058323 A1 | 2/2015 | Bailey |
| 2015/0310524 A1 | 10/2015 | Gospodarek et al. |
| 2016/0125348 A1 | 5/2016 | Dyer et al. |

FOREIGN PATENT DOCUMENTS

| | | |
|---|---|---|
| EP | 2 613 223 A1 | 7/2013 |
| JP | 2004 207812 A | 7/2004 |
| JP | 2006-158239 A | 6/2006 |
| JP | 2010 193284 A | 9/2010 |
| JP | 2011 139647 A | 7/2011 |
| WO | 98/02037 A1 | 1/1998 |
| WO | 2004/088572 | 10/2004 |
| WO | 2010/056392 | 5/2010 |
| WO | 2012/170163 | 12/2012 |
| WO | 2014/088508 A1 | 6/2014 |
| ZA | 200 308 052 A | 7/2004 |

OTHER PUBLICATIONS

First look at new Mio Link ANT +/Bluetooth Smart optical heart rate wrist band; http://www.dcrainmaker.com/2014/01/mio-link-first-look.html; Jan. 6, 2014 (accessed Apr. 19, 2016).

SAS, "SAS BI Dashboard 4.31 User's Guide", Second Edition, by SAS Electronic book, Aug. 1, 2012, downloaded at http://support.sas.com/documentation/cdl/en/bidbrdug/ 65580/PDF/default/bidrdrug.pdf.

PCT International Search Report and Written Opinion; PCT/IB2013/060285, dated Feb. 18, 2014.

PCT International Search Report and Written Opinion; PCT/IB2014/063974, dated Dec. 2, 2014.

PCT International Search Report and Written Opinion; PCT/IB2014/063975, dated Dec. 3, 2014.

PCT International Search Report and Written Opinion; PCT/IB2014/063976, dated Dec. 12, 2014.

PCT International Search Report and Written Opinion; PCT/IB2014/063979, dated Jan. 7, 2015.

PCT International Search Report and Written Opinion; PCT/IB2014/063980, dated Jan. 5, 2015.

PCT International Search Report and Written Opinion; PCT/IB2014/063982, dated Dec. 22, 2014.

PCT International Search Report and Written Opinion; PCT/US2013/047645, dated Sep. 27, 2013.

PCT International Search Report and Written Opinion; PCT/US2013/047869, dated Oct. 21, 2013.

PCT International Search Report and Written Opinion; PCT/US2013/047926, dated Oct. 11, 2013.

PCT International Search Report and Written Opinion; PCT/US2013/048129, dated Oct. 17, 2013.

PCT International Search Report and Written Opinion; PCT/US2013/048177, dated Oct. 21, 2013.

PCT International Search Report and Written Opinion; PCT/IB2014/063973, dated Nov. 28, 2014.

PCT International Search Report and Written Opinion; PCT/IB2014/063981, dated Feb. 10, 2015.

PCT International Search Report and Written Opinion; PCT/IB2014/063978, dated Dec. 19, 2014.

PCT International Search Report and Written Opinion; PCT/IB2014/063977, dated Nov. 28, 2014.

PCT International Search Report and Written Opinion; PCT/IB2014/063983; Mar. 5, 2015.

Allen, et al; Upper Extremity Kinematic Trends of Fly-Fishing; Establishing the Effects of Line Length; Sports Biomechanics; vol. 7, No. 1; pp. 38-53; Jan. 2008.

* cited by examiner

MOTION CAPTURE WHILE FISHING

CROSS-REFERENCE TO RELATED APPLICATIONS

This application claims the benefit of U.S. Provisional Patent Application Ser. No. 61/868,444, filed Aug. 21, 2013 and titled FISHING DATA COLLECTION AND USE, the disclosure of which is incorporated herein by reference.

BACKGROUND

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Accurate data, including, for example, a count of fishing casts made, can be very useful for a fisherman. A device that can capture this data can provide advantages to a fisherman. Such advantages include requiring less time to record information, and collecting more accurate data.

SUMMARY

Described herein are implementations of various technologies for a method for analyzing motion capture data to detect a cast, catch, or bite. In one implementation, a non-transitory computer-readable medium having stored thereon computer-executable instructions which, when executed by a computer, cause the computer to perform various actions. The actions may include receiving motion capture data recorded by one or more cameras. The actions may include analyzing the motion capture data to detect a cast, catch, or bite. The actions may also include storing a record of the cast, catch, or bite.

Described herein are also implementations of various technologies for a method for analyzing a three dimensional scan of a fish to determine a length and weight of the fish. In one implementation, a non-transitory computer-readable medium having stored thereon computer-executable instructions which, when executed by a computer, cause the computer to perform various actions. The actions may include receiving a three dimensional scan of a fish. The actions may include analyzing the three dimensional scan to determine a length and weight of the fish. The actions may also include storing a record of the length and weight of the fish.

Described herein are also implementations of various technologies for a method for analyzing motion capture data to automatically detect casts, catches, or bites. In one implementation, a non-transitory computer-readable medium having stored thereon computer-executable instructions which, when executed by a computer, cause the computer to perform various actions. The actions may include receiving motion capture data recorded by one or more cameras, wherein the motion capture data comprises motions of a fisherman during a fishing trip. The actions may include analyzing the motion capture data to automatically detect casts, catches, bites, or combinations thereof performed by a fisherman during a fishing trip. The actions may also include storing a record of the casts, catches, or bites.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various techniques will hereafter be described with reference to the accompanying drawings. It should be understood, however, that the accompanying drawings illustrate only the various implementations described herein and are not meant to limit the scope of various techniques described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Various implementations of motion capture while fishing described herein will now be described in more detail with reference to FIGS. 1-7.

Figure 1:
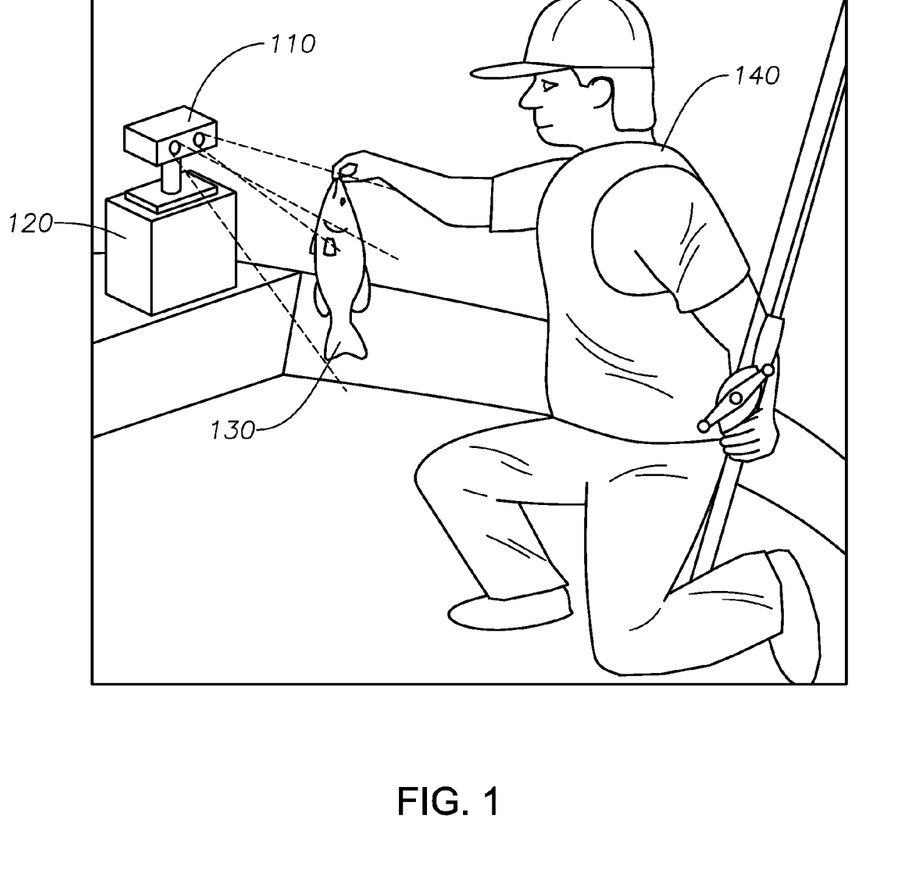
FIG. 1 illustrates using a motion capture device to capture fishing data in accordance with implementations of various techniques described herein.
Figure 7:
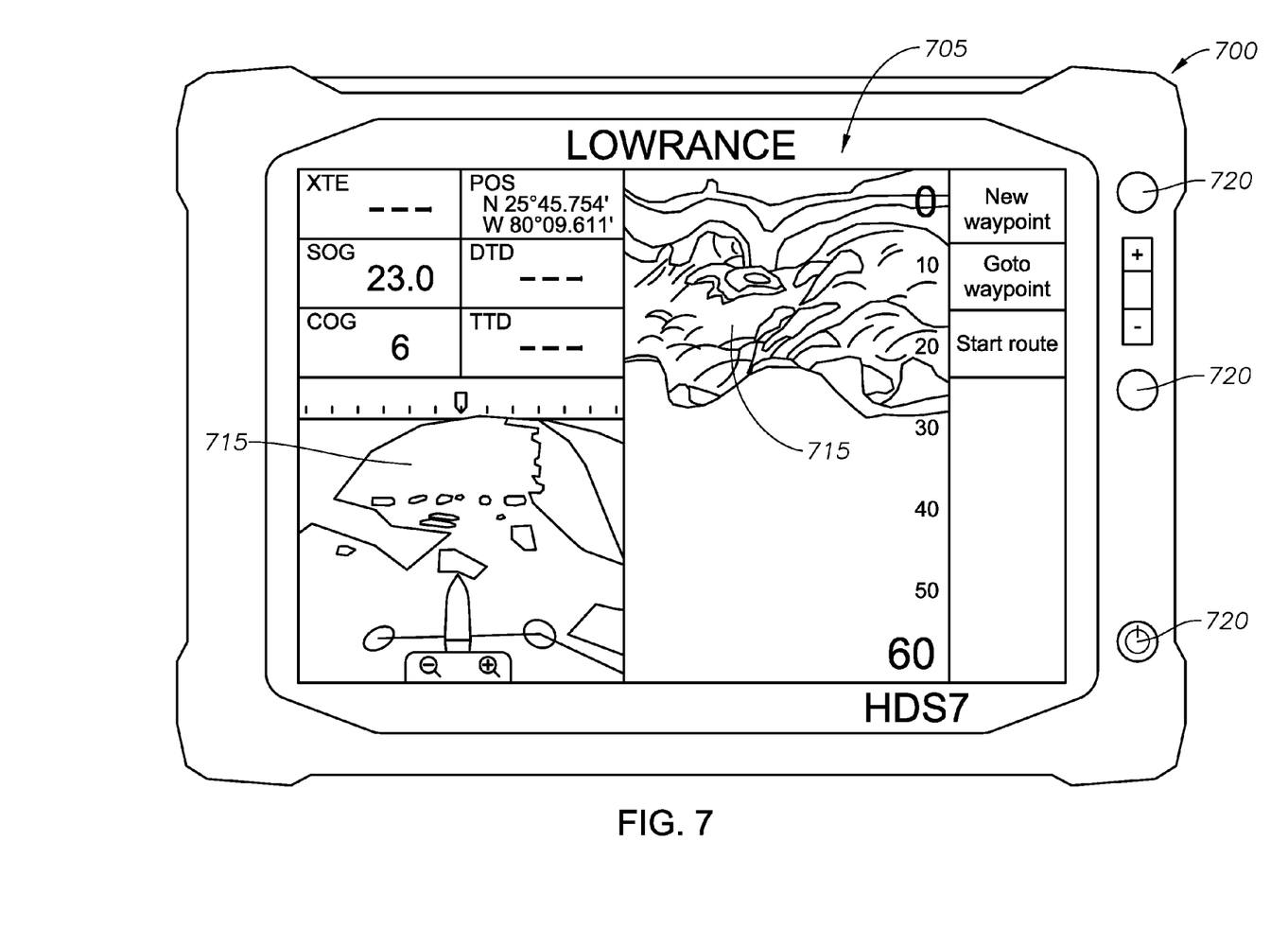
FIG. 7 illustrates a schematic of a marine electronics device in accordance with implementations of various techniques described herein.

FIG. 1 illustrates using a motion capture device to capture fishing data in accordance with implementations of various techniques described herein. In FIG. 1, a marine electronics device 120, further described in FIG. 7, is used to collect fishing data, such as a record of casts, catches, bites, or other events that may occur during a fishing trip.

Attached to the marine electronics device 120 is a motion capture device 110. The motion capture device 110 includes one or more cameras that may be used to capture motion data during a fishing trip. The cameras may capture images, videos, or both. The cameras may also be used to capture depth data. For example, if a fisherman is fishing in front of the motion capture device 110, the motion data may include the distance from the motion capture device 110 to the fisherman. In one implementation, the motion capture device 110 may monitor a plurality of tracking points located on a body, a fishing rod, or points on a fish. For example, a fisherman's elbow may be a tracking point. As the fisherman moves his elbow, the motion capture device 110 would detect the motion of the tracking point. The location for tracking points may be selected by identifying specific patterns or structures. In one implementation, a fisherman may wear one or more devices with sensors, such as accelerometers, and the sensor data may be used in combination with the data captured by the cameras in the motion capture device 110.

Although the motion capture device 110 is illustrated in FIG. 1 as a device attached to the marine electronics device 120, other implementations used to capture motion data are contemplated herein. For example, the cameras may be installed in or mounted on a vessel and positioned to capture video or images from multiple angles. For example, one set of cameras may be positioned at the front of a vessel, and another set of cameras may be positioned at the back of the vessel. In this example, both sets of cameras would be pointed towards the center of the vessel, and would capture video or images of a fisherman from two different angles. In another example, cameras may be located in the marine electronics device 120.

In one implementation, the motion capture device 110 may be used to capture data of a fish 130. In FIG. 1, the motion capture device 110 is performing a three dimensional scan of the fish 130. Data from the motion capture device 110 may then be transmitted to the marine electronics device 120. The marine electronics device 120 may use the three dimensional scan of the fish to estimate a length and weight of the fish 130, and also to determine the species of fish 130.

In another implementation, the motion capture device 110 may be used to capture the motion of a fisherman 140. The motion capture device 110 may then transmit the motion capture data to the marine electronics device 120. The marine electronics device 120 may use the motion capture data to determine the occurrence of a cast, catch, bite, or other fishing event. The motion capture device 110 may also use the motion capture data to determine the type of cast or other data related to the fishing event.

Figure 2:
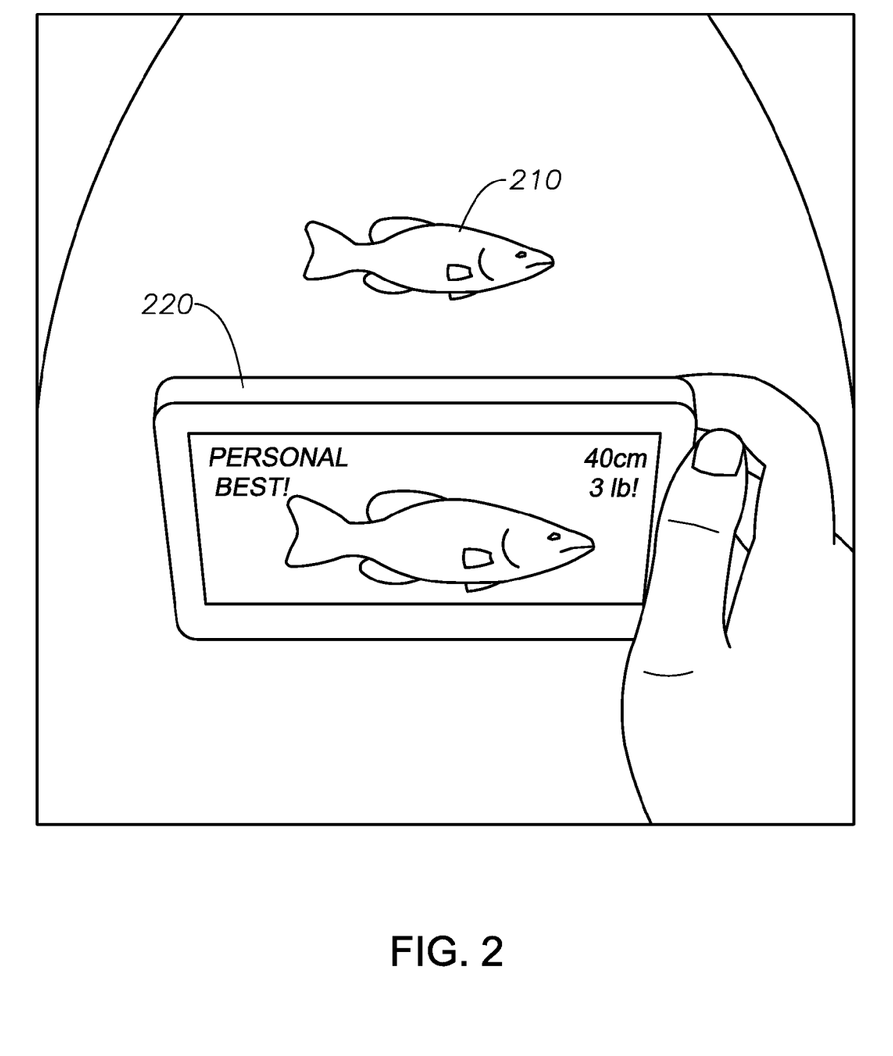
FIG. 2 illustrates using a three dimensional scanner to capture fishing data in accordance with various implementations described herein.

FIG. 2 illustrates using a three dimensional scanner to capture fishing data in accordance with various implementations described herein. In FIG. 2, a smart phone 220 has one or more cameras. The cameras in the smart phone 220 may be used to take a picture of a fish 210, or to perform a three dimensional scan of a fish 210. The image or three dimensional scan of the fish 210 may then be analyzed by the smartphone 220 and used to estimate the length of the fish 210, weight of the fish 210, or the species of fish 210.

Figure 3:
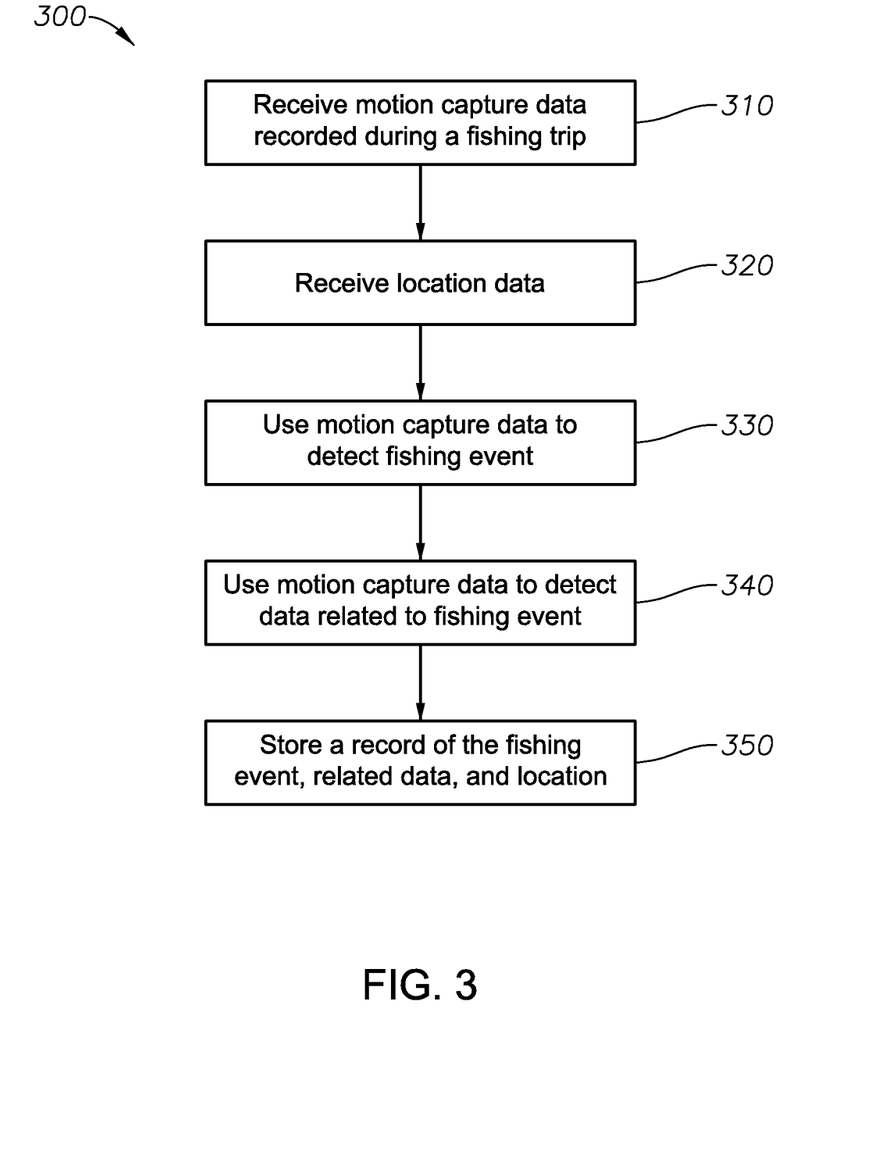
FIG. 3 is a flow diagram for a method of detecting fishing data in accordance with implementations of various techniques described herein.
Figure 6:
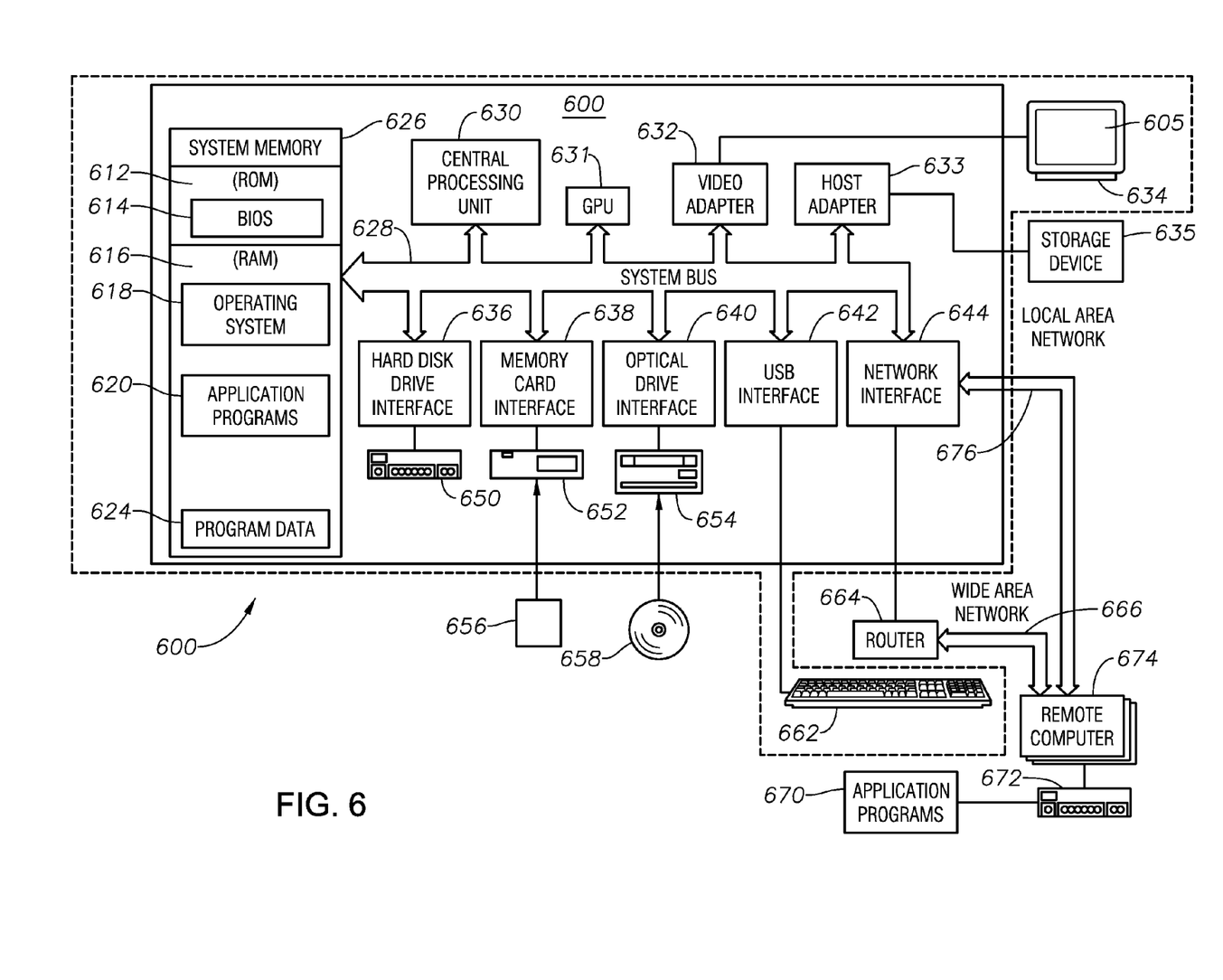
FIG. 6 illustrates a schematic diagram of a computing system in which the various technologies described herein may be incorporated and practiced.

FIG. 3 is a flow diagram for a method 300 of detecting fishing data in accordance with implementations of various techniques described herein. In one implementation, method 300 may be performed by any computer system 600, including a portable computer system, a smart phone device, a remote server, a marine electronics device 700, a cloud server and the like. It should be understood that while method 300 indicates a particular order of execution of operations, in some implementations, certain portions of the operations might be executed in a different order, and on different systems. Further, in some implementations, additional operations or steps may be added to the method 300. Likewise, some operations or steps may be omitted.

At block 310, method 300 may receive motion capture data recorded during a fishing trip. The motion capture data may be recorded using a motion capture device 110, as illustrated in FIG. 1. The motion capture data may include motions performed by a fisherman during a fishing trip, such as casting, making catches, or any other motions performed by the fisherman during the fishing trip.

At block 320, method 300 may receive location data. The location data may be recorded using a Global Positioning System (GPS). The GPS may be located in a marine electronics device 700, or located on a vessel and connected to the marine electronics device 700. The location data may describe the approximate position of a vessel or fisherman.

At block 330, method 300 may analyze the motion capture data received at block 310 to detect one or more fishing events. The fishing events may include casts, catches, bites, fish on the line, fish off the line, start of a fight, end of a fight, or other events that occur during a fishing trip. In one implementation, the motion capture data received at block 310 may be compared to previously recorded motion capture data. For example, the motion capture data may be compared to previously recorded motion capture data of fishermen making casts. In another implementation, the speed and direction of motion in the motion capture data may be analyzed to detect a fishing event.

At block 340, method 300 may use the motion capture data received at block 310 to detect data related to the fishing event detected at block 330. This step is optional. For example, if a cast is detected at block 330, at block 340, the type of cast or type of equipment (e.g., lure, rod, etc.) used may be detected. In another example, if a catch is detected at block 330, the species of the caught fish may be detected, the length of fight may be detected, or the length of the caught fish may be detected at block 340.

At block 350, a record of the fishing event detect at block 330, any related data detected at block 340, and the location received at block 320 may be stored to memory. In one implementation, the record may be transmitted to a cloud software service. In another implementation, the record may include a timestamp in addition to or instead of a location.

Method 300 may be used continuously during a fishing trip to record fishing events throughout the fishing trip. For example, a motion capture device may be activated at the beginning of a fishing trip and deactivated at the end of the fishing trip. In this example, method 300 may continuously analyze motion capture data recorded by the motion capture device and record fishing events as they occur. In this manner, fishing events would be automatically detected and recorded during a fishing trip without any user input.

Figure 4:
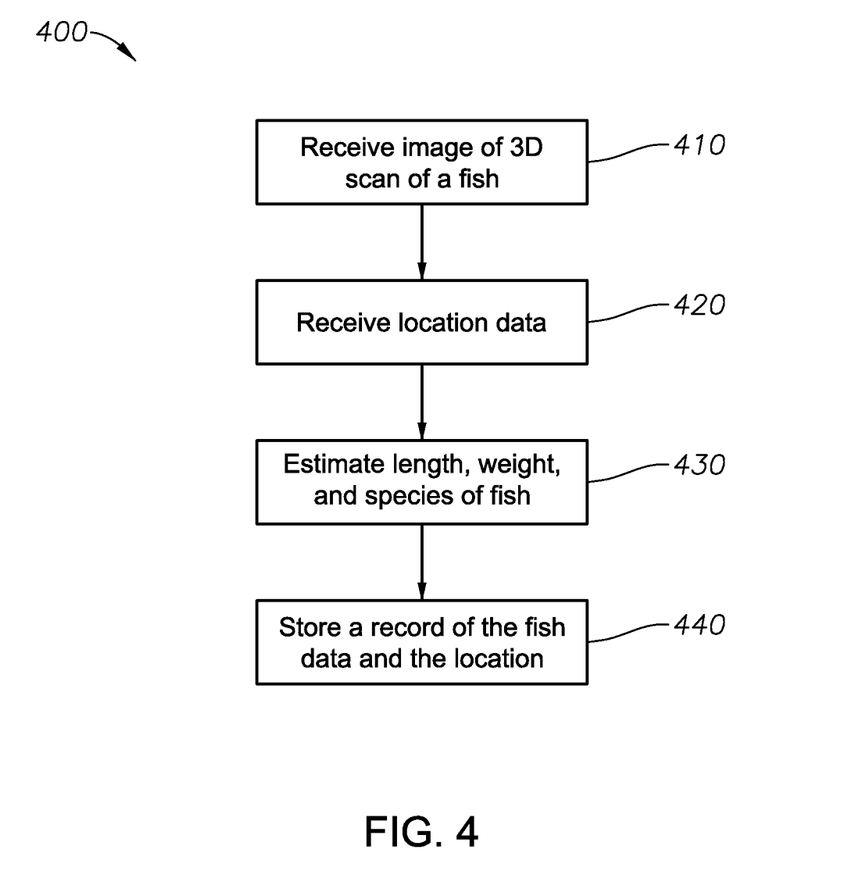
FIG. 4 is a flow diagram for a method of using a three dimensional scan of a fish to record fishing data in accordance with implementations of various techniques described herein.

FIG. 4 is a flow diagram for a method of using a three dimensional scan of a fish to record fishing data in accordance with implementations of various techniques described herein. In one implementation, method 400 may be performed by any computer system 600, including a portable computer system, a smart phone device, a remote server, a marine electronics device 700, a cloud server and the like. It should be understood that while method 400 indicates a particular order of execution of operations, in some implementations, certain portions of the operations might be executed in a different order, and on different systems. Further, in some implementations, additional operations or steps may be added to the method 400. Likewise, some operations or steps may be omitted.

At block 410, method 400 may receive an image of a fish or a three dimensional scan of a fish. The image or scan may be captured using one or more cameras. FIGS. 1 and 2 illustrate examples of capturing images and three dimensional scans of fish. A three dimensional scan of a fish may include data describing the shape and color of a fish. For example, the three dimensional scan may be a point cloud in a three dimensional coordinate system. A point cloud is a set of data points in a coordinate system. For example, if the point cloud coordinate system is a three dimensional coordinate system, the set of data points may form a three dimensional object. In this example, the data points may describe the shape and volume of a three dimensional object.

At block 420, method 400 may receive location data. The location data may be recorded using a GPS. The GPS may be located in a marine electronics device 700, or located on a vessel and connected to the marine electronics device 700. The location data may describe the approximate position of a vessel or fisherman.

At block 430, method 400 may use the scan or image received at block 410 to estimate a length and weight of the fish. In one implementation, the length may be determined using the scan or image, and then the weight may be estimated using the length.

The scan or image received at block 410 may also be used at block 430 to determine the species of the fish. In one implementation, method 400 may compare the image or scan of the fish to stored images or scans of previously caught and identified fish, and determine which stored image or scan is most similar to the image or scan received at block 410. The location received at block 420 may also be used when determining the species of fish. For example, the location may be used to determine which species of fish are likely to inhabit the location of a caught fish, and then the scan or image of the caught fish may be used to determine which of those species has a similar appearance to the caught fish.

At block 440, method 400 may store a record of the fish data determined at block 430, and the location received at block 420, to memory. In one implementation, the record may be transmitted to a cloud software service. In a second implementation, the record may include a timestamp in addition to or instead of a location.

In one implementation, method 400 may be activated continuously throughout a fishing trip. For example, at the beginning of a fishing trip a motion capture device may be activated, and at the end of a fishing trip, the motion capture device may be deactivated. In this example, whenever a fisherman catches a fish, the fish may be scanned and an estimate of the length, weight and species may be automatically determined and recorded.

In another implementation, method 400 may be implemented as an application on a smart phone device. After a fisherman catches a fish, the fisherman may activate the application on the smart phone and take a picture or perform a three dimensional scan of the fish. The length, weight and species of the fish may then be automatically determined and recorded.

In yet another implementation, method 400 may be used during a fishing competition to ensure that accurate data describing a catch is recorded. For example, method 400 may be used to confirm measurements made by a competitor in a fishing competition.

Figure 5:
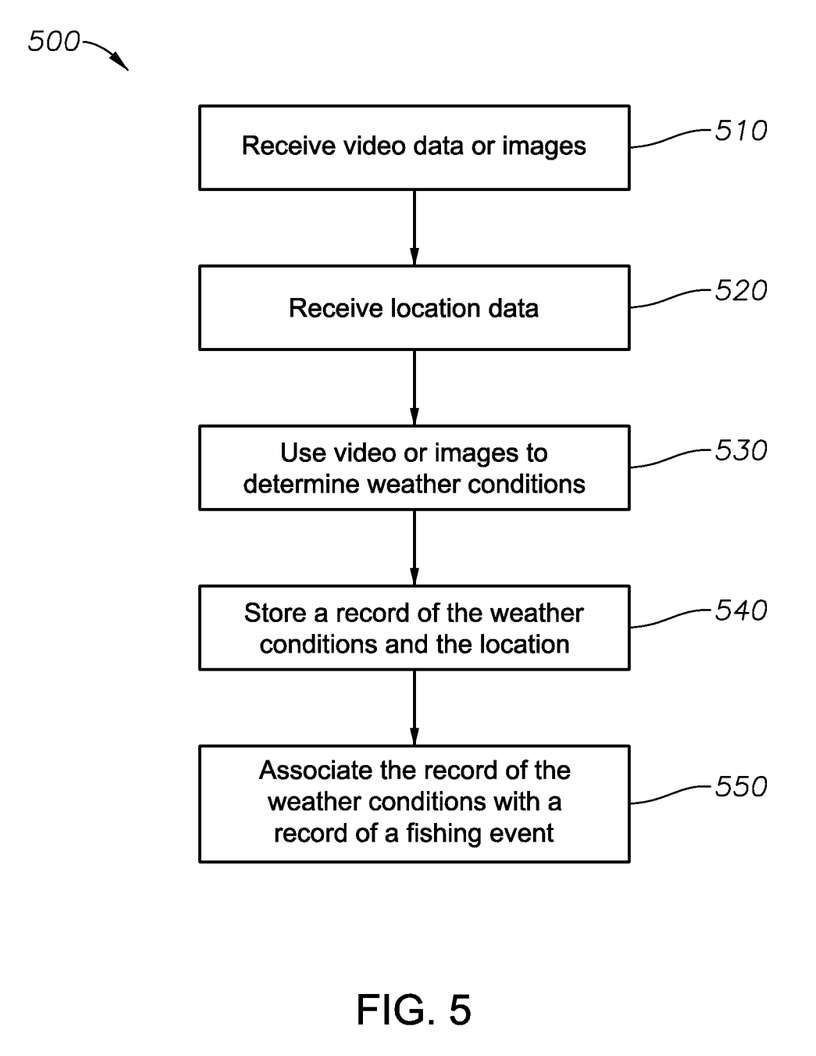
FIG. 5 is a flow diagram for a method of recording weather conditions in accordance with implementations of various techniques described herein.

FIG. 5 is a flow diagram for a method 500 of recording weather conditions in accordance with implementations of various techniques described herein. In one implementation, method 500 may be performed by any computer system 600, including a portable computer system, a smart phone device, a remote server, a marine electronics device 700, a cloud server and the like. It should be understood that while method 500 indicates a particular order of execution of operations, in some implementations, certain portions of the operations might be executed in a different order, and on different systems. Further, in some implementations, additional operations or steps may be added to the method 500. Likewise, some operations or steps may be omitted.

At block 510, method 500 may receive video data or images. The video data or images may be recorded using a motion capture device, such as the motion capture device 110 illustrated in FIG. 1. The video data or images may be captured using any other camera system. For example, a camera pointing directly towards the sky may be used to capture the video data or images.

At block 520, method 500 may receive location data. The location data may be recorded using a GPS. The GPS may be located in a marine electronics device 700, or located on a vessel and connected to the marine electronics device 700. The location data may describe the approximate position of a vessel or fisherman.

At block 530, method 500 may use the video or images received at block 510 to determine weather conditions. The video or images may be used to determine cloud clover, light levels, precipitation, or other weather conditions relevant to a fisherman.

At block 540, a record of the weather conditions determined at block 530, and the location received at block 520 may be stored in memory. Additional environmental information may be determined using a marine electronics device 700, smart phone device, or other device and stored as well, such as tidal information, atmospheric temperature, water temperature, current, moon phase, wind speed and direction, or any other environmental data. In one implementation, the record may be transmitted to a cloud software service. In another implementation, the record may include a timestamp in addition to or instead of a location. In yet another implementation, weather condition data may be recorded throughout a fishing trip, or at predetermined intervals, and stored in memory.

At block 550, the record of the weather conditions may be associated with a record of a fishing event. For example, when a catch occurs, a record of the catch may be stored, and a record of the weather conditions at the time of the catch may be stored and associated with the record of the catch. In one implementation, the record of the weather conditions may be combined with the record of the fishing event.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, tablets, wearable computers, cloud computing systems, virtual computers, marine electronics devices, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may be implemented in the context of marine electronics, such as devices found in marine vessels and/or navigation systems. Ship instruments and equipment may be connected to the computing systems described herein for executing one or more navigation technologies. As such, the computing systems may be configured to operate using sonar, radar, GPS and like technologies.

The various technologies described herein may also be implemented in distributed computing environments where tasks are performed by remote processing devices that are linked through a communications network, e.g., by hard-wired links, wireless links, or combinations thereof. In a distributed computing environment, program modules may be located in both local and remote computer storage media including memory storage devices.

FIG. 6 illustrates a computer system 600 into which implementations of various technologies and techniques described herein may be implemented. Computing system 600 may be a conventional desktop, a handheld device, a wearable device, a controller, a personal digital assistant, a server computer, an electronic device/instrument, a laptop, a tablet, or part of a navigation system, marine electronics, or sonar system. It should be noted, however, that other computer system configurations may be used.

The computing system 600 may include a central processing unit (CPU) 630, a system memory 626 and a system bus 628 that couples various system components including the system memory 626 to the CPU 630. Although only one CPU 630 is illustrated in FIG. 6, it should be understood that in some implementations the computing system 600 may include more than one CPU 630.

The CPU 630 can include a microprocessor, a microcontroller, a processor, a programmable integrated circuit, or a combination thereof. The CPU 630 can comprise an off-the-shelf processor such as a Reduced Instruction Set Computer (RISC), including an Advanced RISC Machine (ARM) processor, or a Microprocessor without Interlocked Pipeline Stages (MIPS) processor, or a combination thereof. The CPU 630 may also include a proprietary processor. The CPU may include a multi-core processor.

The CPU 630 may provide output data to a Graphics Processing Unit (GPU) 631. The GPU 631 may generate graphical user interfaces that present the output data. The GPU 631 may also provide objects, such as menus, in the graphical user interface. A user may provide inputs by interacting with the objects. The GPU 631 may receive the inputs from interaction with the objects and provide the inputs to the CPU 630. In one implementation, the CPU 630 may perform the tasks of the GPU 631. A video adapter 632 may be provided to convert graphical data into signals for a monitor 634. The monitor 634 includes a screen 605. The screen 605 can be sensitive to heat or touching (now collectively referred to as a "touch screen"). In one implementation, the computer system 600 may not include a monitor 634.

The GPU 631 may be a microprocessor specifically designed to manipulate and implement computer graphics. The CPU 630 may offload work to the GPU 631. The GPU 631 may have its own graphics memory, and/or may have access to a portion of the system memory 626. As with the CPU 630, the GPU 631 may include one or more processing units, and each processing unit may include one or more cores.

The system bus 628 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 626 may include a read only memory (ROM) 612 and a random access memory (RAM) 616. A basic input/ output system (BIOS) 614, containing the basic routines that help transfer information between elements within the computing system 600, such as during start-up, may be stored in the ROM 612. The computing system may be implemented using a printed circuit board containing various components including processing units, data storage memory, and connectors.

Certain implementations may be configured to be connected to a GPS and/or a sonar system. The GPS and/or sonar system may be connected via the network interface 644 or Universal Serial Bus (USB) interface 642. In one implementation, the computing system 600, the monitor 634, the screen 605 and buttons may be integrated into a console.

The computing system 600 may further include a hard disk drive 636 for reading from and writing to a hard disk 650, a memory card reader 652 for reading from and writing to a removable memory card 656 and an optical disk drive 654 for reading from and writing to a removable optical disk 658, such as a CD ROM, DVD ROM or other optical media. The hard disk drive 650, the memory card reader 652 and the optical disk drive 654 may be connected to the system bus 628 by a hard disk drive interface 636, a memory card interface 638 and an optical drive interface 640, respectively. The drives and their associated computer-readable media may provide nonvolatile storage of computer-readable instructions, data structures, program modules and other data for the computing system 600.

Although the computing system 600 is described herein as having a hard disk 650, a removable memory card 656 and a removable optical disk 658, it should be appreciated by those skilled in the art that the computing system 600 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, including a Solid State Disk (SSD), CD-ROM, digital versatile disks (DVD), or other optical storage, magnetic cassettes, magnetic tape, magnetic disk storage or other magnetic storage devices, or any other medium which can be used to store the desired information and which can be accessed by the computing system 700. Communication media may embody computer readable instructions, data structures, program modules or other data in a modulated data signal, such as a carrier wave or other transport mechanism and may include any information delivery media. By way of example, and not limitation, communication media may include wired media such as a wired network or direct-wired connection, and wireless media such as acoustic, RF, infrared and other wireless media. The computing system 600 may also include a host adapter 633 that connects to a storage device 635 via a small computer system interface (SCSI) bus, a Fiber Channel bus, an eSATA bus, or using any other applicable computer bus interface. The computing system 600 can also be connected to a router 664 to establish a wide area network (WAN) 666 with one or more remote computers 674. The router 664 may be connected to the system bus 628 via a network interface 644. The remote computers 674 can also include hard disks 672 that store application programs 670.

In another implementation, the computing system 600 may also connect to one or more remote computers 674 via local area network (LAN) 676 or the WAN 666. When using a LAN networking environment, the computing system 600 may be connected to the LAN 676 through the network interface or adapter 644. The LAN 676 may be implemented via a wired connection or a wireless connection. The LAN 676 may be implemented using Wi-Fi technology, cellular technology, or any other implementation known to those skilled in the art. The network interface 644 may also utilize remote access technologies (e.g., Remote Access Service (RAS), Virtual Private Networking (VPN), Secure Socket Layer (SSL), Layer 2 Tunneling (L2T), or any other suitable protocol). These remote access technologies may be implemented in connection with the remote computers 674. It will be appreciated that the network connections shown are exemplary and other means of establishing a communications link between the computer systems may be used. The network interface 644 may also include digital cellular networks, Bluetooth, or any other wireless network interface.

A number of program modules may be stored on the hard disk 650, memory card 656, optical disk 658, ROM 612 or RAM 616, including an operating system 618, one or more application programs 620, program data 624 and a database system. The one or more application programs 620 may contain program instructions configured to perform methods 300, 400, or 500 according to various implementations described herein. The operating system 618 may be any suitable operating system that may control the operation of a networked personal or server computer, such as Windows® XP, Mac OS® X, Unix-variants (e.g., Linux® and BSD®), Android®, iOS®, and the like.

A user may enter commands and information into the computing system 600 through input devices such as a keyboard 662 and pointing device. Other input devices may include a microphone, joystick, game pad, satellite dish, scanner, user input button, wearable device, or the like. These and other input devices may be connected to the CPU 630 through a USB interface 642 coupled to system bus 628, but may be connected by other interfaces, such as a parallel port, Bluetooth or a game port. A monitor 605 or other type of display device may also be connected to system bus 628 via an interface, such as a video adapter 632. In addition to the monitor 634, the computing system 600 may further include other peripheral output devices such as speakers and printers.

Marine Electronics Device

FIG. 7 illustrates a schematic diagram of a marine electronics device 700 in accordance with various implementations described herein. The marine electronics device 700 includes a screen 705. In certain implementations, the screen 705 may be sensitive to touching by a finger. In other implementations, the screen 705 may be sensitive to the body heat from the finger, a stylus, or responsive to a mouse. The device 700 may display marine electronic data 715. The marine electronic data types 715 may include chart data, radar data, sonar data, steering data, dashboard data, navigation data, fishing data, and the like. The marine electronics device 700 may also include a plurality of buttons 720, which may be either physical buttons or virtual buttons, or a combination thereof. The marine electronics device 700 may receive input through a screen 705 sensitive to touch or buttons 720. The marine electronics device 700 may be connected to a motion capture device using a wired connection, such as USB, or through a wireless connection, such as Bluetooth.

While the foregoing is directed to implementations of various techniques described herein, other and further implementations may be devised without departing from the basic scope thereof, which may be determined by the claims that follow.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A non-transitory computer-readable medium having stored thereon a plurality of computer-executable instructions which, when executed by a computer, cause the computer to:
receive motion capture data recorded by one or more cameras directed toward a fisherman during a fishing trip, wherein the motion capture data comprises motion of the fisherman during the fishing trip;
analyze the motion capture data to detect an occurrence of a catch;
determine, using a marine electronic device and in response to detecting the occurrence of the catch, a current location of the fisherman;
determine, based on the motion capture data and in response to detecting the occurrence of the catch, fish characteristic data, wherein the fish characteristic data comprises at least one of a species of the caught fish, a length of the caught fish, or the length of fight that resulted in the caught fish; and
store a record of the catch, the current location, and the fish characteristic data in memory.

2. The non-transitory computer-readable medium of claim 1, wherein the motion capture data comprises video of the fisherman.

3. The non-transitory computer-readable medium of claim 1, wherein the motion capture data comprises the location of one or more tracking points on the fisherman's body.

4. The non-transitory computer-readable medium of claim 1, wherein the computer-executable instructions further cause the computer to determine, based on the motion capture data, a type of cast used to catch the fish.

5. The non-transitory computer-readable medium of claim 1, wherein the computer-executable instructions further cause the computer to:
determine, based on the motion capture data and in response to detecting the occurrence of the catch, weather conditions associated with the occurrence of the catch; and
store a record of the weather conditions.

6. The non-transitory computer-readable medium of claim 5, wherein the weather conditions comprise cloud cover or light levels.

7. The non-transitory computer-readable medium of claim 1, wherein the computer-executable instructions further cause the computer to transmit the record to a cloud software service.

8. A non-transitory computer-readable medium having stored thereon a plurality of computer-executable instructions which, when executed by a computer, cause the computer to:
receive continuous motion capture data recorded by one or more cameras directed toward a fisherman during a fishing trip, wherein the motion capture data comprises motions of the fisherman during the fishing trip;
analyze the motion capture data to automatically detect the occurrence of catches during the fishing trip;
determine, using a marine electronic device and in response to detecting the occurrence of the catch, a current location of the fisherman; and
store a record of the occurrence of the catches and associated current locations.

9. The non-transitory computer-readable medium of claim 8, wherein the computer-executable instructions further cause the computer to:
determine, based on the motion capture data and in response to detecting the occurrence of the catch, weather conditions associated with the occurrence of the catch; and
associate the corresponding weather conditions with the record of the occurrence of the catches.

10. The non-transitory computer-readable medium of claim 8, wherein the computer-executable instructions further cause the computer to:
determine, based on the motion capture data and in response to detecting the occurrence of the catch, fish characteristic data, wherein the fish characteristic data comprises at least one of a species of the caught fish, a length of the caught fish, or the length of fight that resulted in the caught fish; and
store a record of the fish characteristic data associated the corresponding occurrence of the catch.

11. The non-transitory computer-readable medium of claim 8, wherein the computer-executable instructions further cause the computer to:
determine, in response to detecting the occurrence of the catch, environment data associated with the occurrence of the catch; and
store a record of the environment data.

12. The non-transitory computer-readable medium of claim 8, wherein the computer-executable instructions further cause the computer to:
determine, in response to detecting the occurrence of the catch, equipment data associated with the occurrence of the catch, wherein the equipment data includes at least one of the type of bait used, the type of lure used, or the type of rod used; and
store a record of the equipment data.

13. The non-transitory computer-readable medium of claim 8, wherein the computer-executable instructions further cause the computer to cause display of the record of the occurrence of the catch and the current location to a user, whereby a user interface presents the record of the catch, the current location, and the fish characteristic data on a screen.

14. The non-transitory computer-readable medium of claim 1, wherein the computer-executable instructions further cause the computer to:
determine, in response to detecting the occurrence of the catch, environment data associated with the occurrence of the catch; and
store a record of the environment data.

15. The non-transitory computer-readable medium of claim 1, wherein the computer-executable instructions further cause the computer to:
determine, in response to detecting the occurrence of the catch, equipment data associated with the occurrence of the catch, wherein the equipment data includes at least one of the type of bait used, the type of lure used, or the type of rod used; and
store a record of the equipment data.

16. The non-transitory computer-readable medium of claim 1, wherein the computer-executable instructions further cause the computer to:
continuously receive motion capture data throughout the fishing trip; and
automatically determine and record fishing event information regarding occurrences of catches during the fishing trip.

17. The non-transitory computer-readable medium of claim 1, wherein the computer-executable instructions further cause the computer to cause display of the record of the catch, the current location, and the fish characteristic data to a user, whereby a user interface presents the record of the catch, the current location, and the fish characteristic data on a screen.

18. An apparatus comprising a processor and memory including computer program code, wherein the computer program code is configured to, with the processor, cause the apparatus to:
  receive motion capture data recorded by one or more cameras directed toward a fisherman during a fishing trip, wherein the motion capture data comprises motion of the fisherman during the fishing trip;
  analyze the motion capture data to detect an occurrence of a catch;
  determine, using a marine electronic device and in response to detecting the occurrence of the catch, a current location of the fisherman;
  determine, based on the motion capture data and in response to detecting the occurrence of the catch, fish characteristic data, wherein the fish characteristic data comprises at least one of a species of the caught fish, a length of the caught fish, or the length of fight that resulted in the caught fish; and
  store a record of the catch, the current location, and the fish characteristic data in memory.

19. The apparatus of claim 18 further comprising a user interface with a screen, wherein the computer program code is further configured to, with the processor, cause the apparatus to cause display of the record of the catch, the current location, and the fish characteristic data to a user, whereby the user interface presents the record of the catch, the current location, and the fish characteristic data on the screen.

\* \* \* \* \*